United States Patent
Dragan et al.

(10) Patent No.: US 6,877,983 B1
(45) Date of Patent: Apr. 12, 2005

(54) DENTAL CAPSULE FOR PLACEMENT OF HIGH VISCOSITY DENTAL COMPOSITE MATERIAL WITH REDUCE EXTRUSION FORCE

(75) Inventors: William B. Dragan, Easton, CT (US); Gordon Rowe, Wallingford, CT (US)

(73) Assignee: Centrix, Inc., Sheldon, CT (US)

( * ) Notice: Subject to any disclaimer, the term of this patent is extended or adjusted under 35 U.S.C. 154(b) by 112 days.

(21) Appl. No.: 10/085,847

(22) Filed: Feb. 27, 2002

Related U.S. Application Data

(63) Continuation-in-part of application No. 09/605,495, filed on Jun. 28, 2000, now Pat. No. 6,379,152, which is a continuation-in-part of application No. 09/552,338, filed on Apr. 19, 2000, now Pat. No. 6,261,094.

(51) Int. Cl.$^7$ ................................. A61C 5/04
(52) U.S. Cl. ........................................... 433/90
(58) Field of Search .................... 433/89, 90; 272/386; 401/176

(56) References Cited

U.S. PATENT DOCUMENTS

| | | | |
|---|---|---|---|
| 2,903,794 A | | 9/1959 | Carfagni |
| 3,521,795 A | | 7/1970 | Langhjelm et al. |
| 3,581,399 A | | 6/1971 | Dragan |
| 3,828,434 A | | 8/1974 | Mosch |
| 4,330,280 A | | 5/1982 | Dougherty et al. |
| 4,384,853 A | | 5/1983 | Welsh |
| 4,391,590 A | | 7/1983 | Dougherty |
| 4,445,626 A | | 5/1984 | Steffen et al. |
| 4,693,684 A | * | 9/1987 | Blatherwick et al. ......... 433/90 |
| 4,767,326 A | | 8/1988 | Bennett et al. |
| 4,801,263 A | | 1/1989 | Clark |
| 4,852,772 A | | 8/1989 | Ennis, III |
| 4,963,093 A | | 10/1990 | Dragan |
| 4,969,816 A | | 11/1990 | Drumm |
| 5,004,124 A | * | 4/1991 | Stefaniak et al. ........... 222/136 |
| 5,052,927 A | * | 10/1991 | Discko, Jr. .................... 433/90 |
| 5,083,921 A | | 1/1992 | Dragan |
| 5,100,320 A | | 3/1992 | Martin et al. |
| 5,122,057 A | | 6/1992 | Discko, Jr. |
| 5,129,825 A | | 7/1992 | Discko, Jr. |
| 5,165,890 A | | 11/1992 | Discko, Jr. |
| 5,172,807 A | | 12/1992 | Dragan et al. |
| 5,322,440 A | | 6/1994 | Steele |
| 5,421,663 A | | 6/1995 | Bravo |
| 5,460,523 A | | 10/1995 | Schulman |
| 5,591,027 A | | 1/1997 | Muhlbauer |
| 5,707,234 A | | 1/1998 | Bender |
| 5,722,830 A | | 3/1998 | Brandhorst et al. |
| 5,893,714 A | | 4/1999 | Arnold et al. |
| 5,938,439 A | * | 8/1999 | Mertins et al. ............... 433/90 |
| 6,099,307 A | * | 8/2000 | Discko, Jr. .................... 433/90 |
| 6,102,699 A | | 8/2000 | Galehr et al. |
| 6,261,094 B1 | | 7/2001 | Dragan |

* cited by examiner

*Primary Examiner*—Todd E. Manahan
(74) *Attorney, Agent, or Firm*—Fattibene & Fattibene; Paul A. Fattibene; Arthur T. Fattibene

(57) ABSTRACT

A dental capsule for extruding high viscosity dental material providing reduced extrusion force. The dental capsule comprises a body portion, a transition portion and a discharge portion. The transition portion has an axis having an angular relationship with the axis of the body portion and the axis of the discharge portion. This relationship and transitional portion reduces the extrusion force required in extruding high viscosity dental material. In another embodiment of the present invention, a flexible piston having a conical front end is utilized to more fully extrude the dental material from the dental capsule. The dental capsule may have flexible walls with the flexible piston and walls cooperating to extrude substantially all of the dental material. The present invention, when used with high viscosity dental materials, results in less extrusion force required and does not damage the dental material during extrusion.

17 Claims, 2 Drawing Sheets

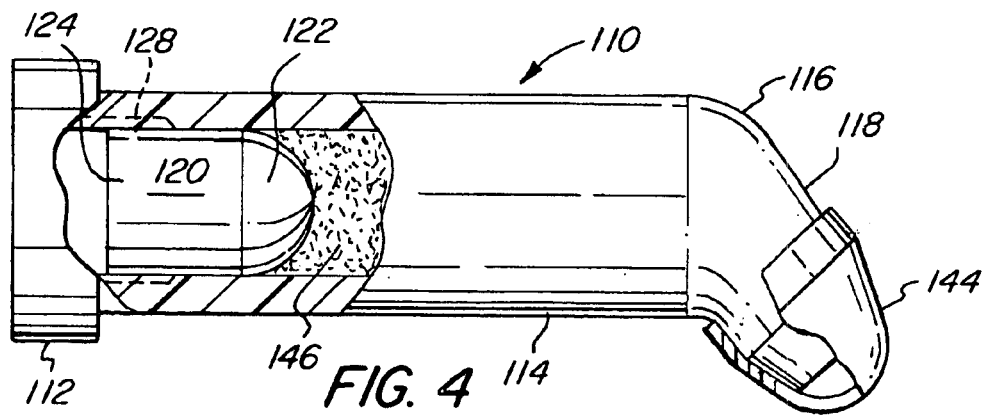
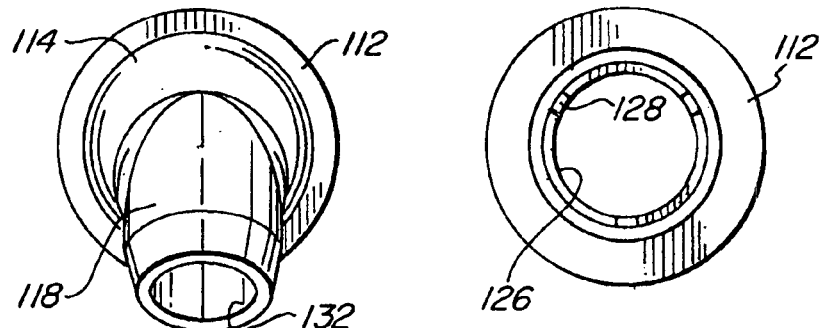
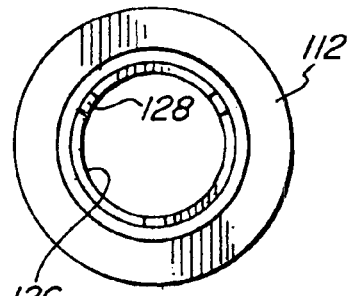
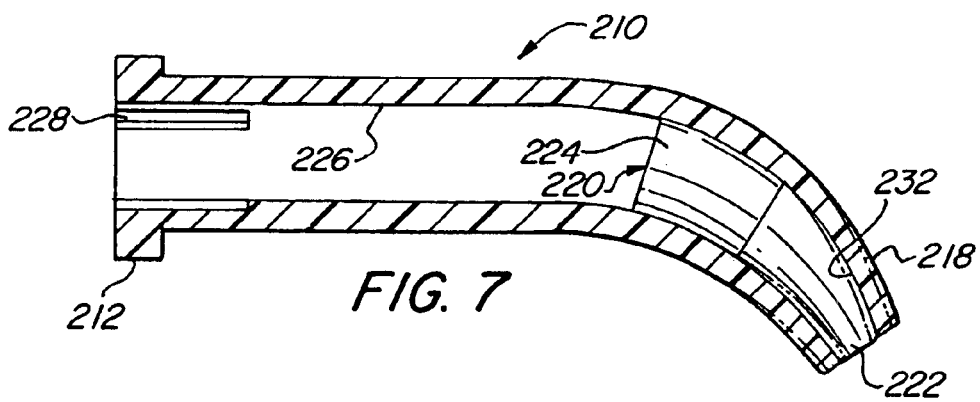
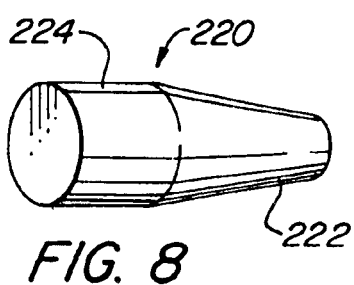

DENTAL CAPSULE FOR PLACEMENT OF HIGH VISCOSITY DENTAL COMPOSITE MATERIAL WITH REDUCE EXTRUSION FORCE

RELATED APPLICATIONS

This is a continuation in part application of application Ser. No. 09/605,495 filed Jun. 28, 2000 now U.S. Pat. No. 6,379,752, which is a continuation in part of application Ser. No. 09/552,338 filed Apr. 19, 2000, now U.S. Pat. No. 6,261,094, both of which are herein incorporated by reference in their entirety.

FIELD OF THE INVENTION

The present invention relates generally to a dental capsule used in the placement of a high viscosity composite restorative dental material, and more specifically to a unit dose dental capsule having an internal configuration and a piston that provides a reduced force for extruding the high viscosity dental material.

BACKGROUND OF THE INVENTION

Dental composites have been used for many years for restoring teeth. Initially, restorative materials were placed in a cavity of a tooth with a spatula or other packing dental instrument. It became desirable to dispense the composite materials with a capsule and syringe for ease of dispensing and to avoid air bubbles or voids from forming, as often occurred with the spatula packing techniques. However, as the dental composite materials changed and improved, the viscosity and thixotropic nature of the dental composite material created problems in the dispensing thereof in a capsule. Many of the preferred composite materials became too viscous for easy dispensing with a capsule. Often, the force required to dispense the high viscosity dental composite materials would make its placement difficult for the dentist, as well as possibly damaging or changing the physical properties of the dental composite material. Therefore, there is a need to provide a dental capsule that can dispense high viscosity dental composite materials with a reduced force and less likelihood of damaging the high viscosity dental composite material.

SUMMARY OF THE INVENTION

The present invention comprises a dental capsule having a body portion, a transition portion, and a discharge portion. The body portion has a body axis and the transition portion has a transition axis angularly disposed with respect to the body axis. The discharge portion has a discharge axes that is angularly disposed with respect to the transition axis. A piston having a conical portion and a cylindrical portion, which is flexible is used to navigate the transition portion and dispense nearly all of the dental material contained within the capsule.

In another embodiment of the invention, the capsule is made of a flexible material such that the discharge portion expands slightly when a conical shaped piston is force there through.

Accordingly, it is an object of the present invention to dispense high viscosity dental material with less extrusion force.

It is another object of the present invention to efficiently dispense high viscosity dental material in a unit dose capsule.

It is an advantage of the present invention that substantially all of the dental material is extruded.

It is a further advantage of the present invention that the dental material is less likely to be damaged due to the forces of extrusion.

It is a feature of the present invention that different axes are used for the body portion, transition portion and the discharge portion of the capsule.

It is a further feature of the present invention that the capsule has flexible walls in combination with a conical shaped piston.

These and other objects, advantages, and features will become readily apparent in view of the following more detailed description.

BRIEF DESCRIPTION OF THE DRAWINGS

FIG. 4 is an elevational view and partial section illustrating another embodiment of the present invention.

FIG. 5 is a front view of the present invention.

FIG. 6 is a rear view of the present invention.

FIG. 7 is a cross section of another embodiment of the present invention.

FIG. 8 is a perspective view of a piston used in the present invention.

DETAILED DESCRIPTION OF THE PREFERRED EMBODIMENTS

Figure 1:
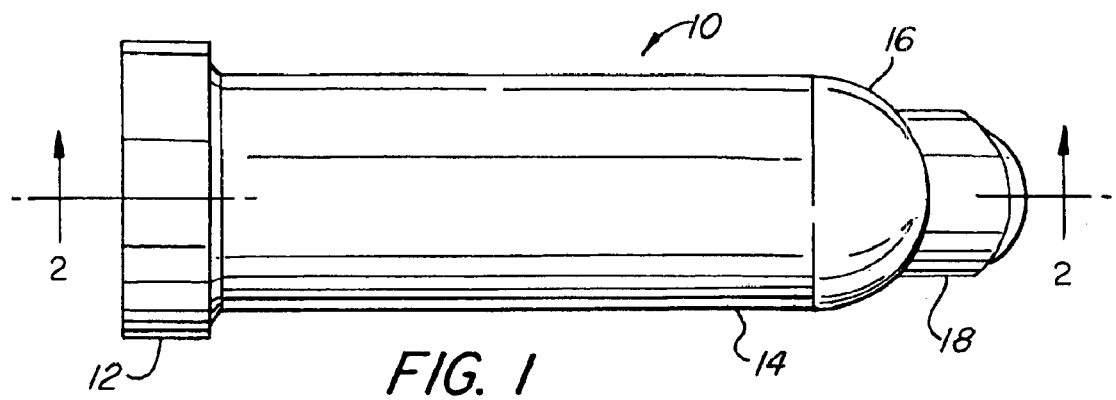
FIG. 1 is a plan view of a dental capsule.

FIG. 1 is a plan view of a dental capsule 10. The dental capsule 10 comprises a flange portion 12, a body portion 14, a transition portion 16, and a discharge portion 18. The capsule 10 may be filled with a high viscosity dental material. The capsule 10 and is dispensed using a syringe which may have a mechanical advantage, such as the syringe disclosed in U.S. Pat. No. 5,489,207 entitled "Dental Cartridge Extruder with Rigid Drop-in Front End" issuing to Dragan et al on Feb. 6, 1996, which is herein incorporated by reference.

Figure 2:
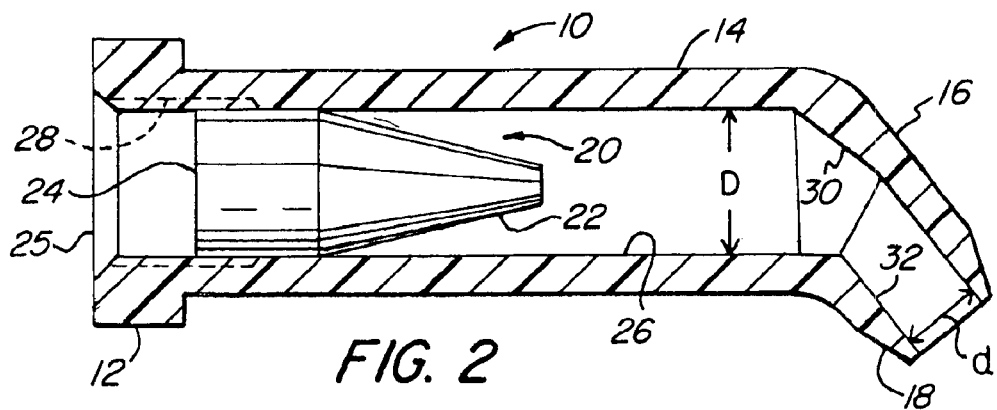
FIG. 2 is a cross section taken along lines 2—2 in FIG. 1.

FIG. 2 more clearly illustrates the internal configuration of the dental capsule of the present invention. A piston 20 having a flexible conical front portion 22 and a cylindrical rear portion 24 is placed within the inside diameter 26 of the body 14 of the cartridge 10. The inside diameter 26 has a diameter D. At the rear of the body portion 14 is opening 25. The piston 20 is placed within the opening 25. Material may be predosed within the body 14. A vent 28 extends longitudinally from the opening 25 and may have a longitudinal extent approximating the axial length of the cylindrical rear portion 24 of the plug or piston 20. The discharge portion 18 has a discharge inside diameter 32 with a diameter d. Between the body inside diameter 26 and the discharge inside diameter 32 is a transition surface 30. The transition surface 30 aids in redirecting the dental material and transitions it for extrusion from the discharge portion 18. The transition surface 30 redirects the dental material and reduces the extrusion forces required to extrude the dental material. Additionally, there are no sharp angles to create a vortex or possible damage the dental material. It has been experimentally determined that the shape of the dental capsule of the present invention reduces extrusion forces by as much as twenty percent in relation to other capsules that do not have the transition portion 16 or the transition surface 30. The piston 20 is illustrated in this embodiment with a conical front portion 22, however, the piston 20 does not need to be conical. The piston 20 only needs to be sufficiently flexible to negotiate around the transition surface 30 inside the transition portion 14.

Figure 3:
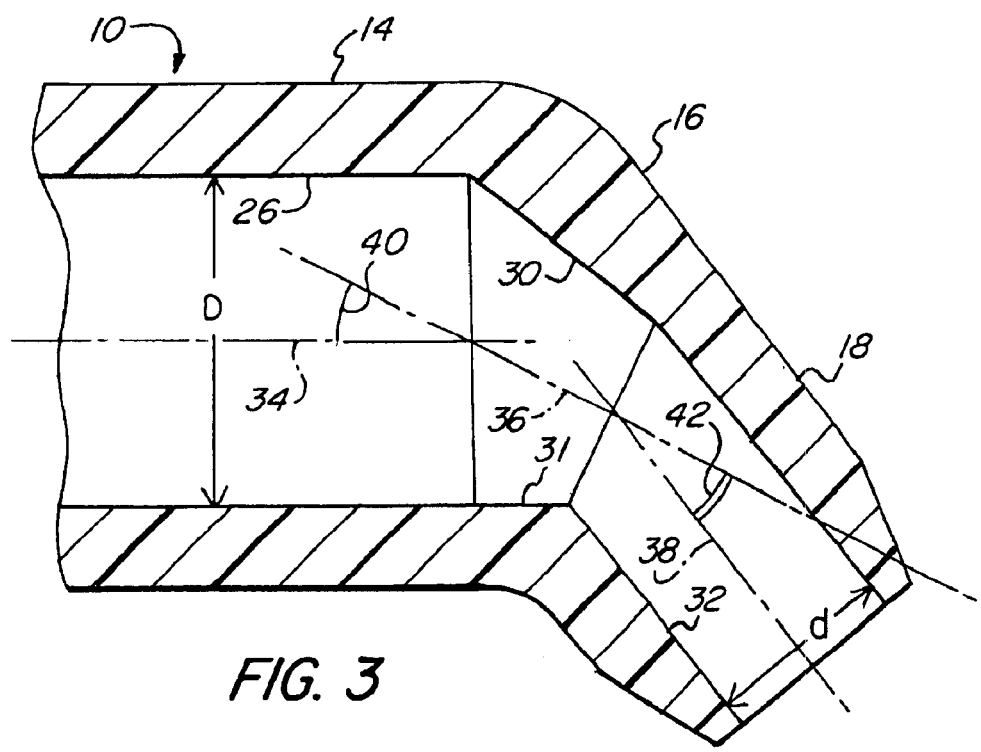
FIG. 3 is an enlarged partial view more clearly illustrating the transition portion of the dental capsule.

FIG. 3 is an enlarged section of the front end of the capsule as illustrated in FIG. 2. In FIG. 3, the transition portion 16 and transition surface 30 can be more clearly seen. FIG. 3 illustrates the relationship between the axes of each portion of the dental capsule 10. The body portion 14 has a substantially constant inside diameter along the inner surface 26. The inside body diameter or inner surface 26 may have a slight release angle to facilitate molding. However, the cylindrical surface 26 has a substantial constant diameter. Line 34 represents the axis of the inside cylindrical surface 26. The transition portion 16 and the transition surface 30 have a conical shape with a non-constant reducing diameter from the body portion 14 to the discharge portion 18. The inside transition surface 30 has an axis 36. The axis 36 intersects with the axis 34 and forms an angle 40 therewith. The angle 40 may range between 25° and 35°, and is preferably 30°. A portion of the transition surface 30 may be coincident with a portion of the body inside surface 26, for example, at lower segment 31. The inside discharge surface 32 has an axis 38. The inside discharge surface 32 has a substantially constant diameter d. The discharge axis 38 intersects with the transition axis 36 at angle 42. Angle 42 may range between 15° and 25°, and is preferably 19.5°. In the preferred embodiment where the angle 40 is 30° and the angle 42 is 19.5°, it has been experimentally determined that for the same dental composite material, the extrusion forces have been reduced approximately twenty percent from prior dental capsule configurations without a transition portion 16. High extrusion forces may damage dental material by shearing the material or forcing components of the composite dental material to separate affecting its properties.

FIG. 4 illustrates another embodiment of the present invention where a different shaped piston 120 is used. The capsule 110 has a flange 112, a body portion 114, a transition portion 116, and a discharge portion 118. A cap 144 seals the discharge portion 118. A vent 128 is formed adjacent the rear opening of the capsule 110. Material 146 is placed within the body portion 114 of the capsule 110. The dental material 146 is preferably an ultra high viscosity dental material having filler greater than fifty percent by volume. In this embodiment, the piston 120 has a cylindrical rear portion 124 and a hemispherical front portion 122. The hemispherical front portion 122 may be made of a flexible material so as to conform to the shape of the transition portion 116.

FIG. 5 is a front elevational view of the embodiment illustrated in FIG. 4. The inside discharge surface 132 at the end of the discharge portion 118 can be more clearly seen.

FIG. 6 is a rear elevational view of the embodiment illustrated in FIG. 4. The vents 128 formed within the inside surface 126 of the body portion can more clearly be seen. The vents 128 aid in the placement of the piston 120 in the body portion 114 without placing pressure on the dental material 146 placed therein.

FIG. 7 is a cross section illustrating another embodiment of the present invention. In this embodiment, the dental capsule 210 is made of a flexible plastic or rubber type material that is permitted to expand when a force is applied. The dental capsule 210 has a flange 212 and an inside body surface 226. The inside body surface 226 is substantially cylindrical and has a substantially constant diameter. The piston 220 has a substantially cylindrical portion 224 and a conical portion 222. The piston 220 is made of a flexible material. The conical portion 222 of the piston 220 is sufficiently flexible to easily negotiate around a curved surface. The piston 220 is forced down the capsule 210 to extrude a viscous dental material. As the piston 220 advances to the discharge end 218 of the capsule 210, the conical front end portion 222 of the piston 220 forces the flexible walls of the discharge portion 218 outward. The conical front end portion 222 is also made of a flexible material to conform to the curved shape of the discharge end 218. The conical front end portion also has a diameter larger than the inside diameter of the discharge end 218. This embodiment of the present invention permits substantially all of the dental material to be extruded from the dental capsule 210.

FIG. 8 is a perspective view illustrating the piston 220 outside of the dental capsule 210, illustrated in FIG. 7. The shape of the piston 220 is clearly illustrated in FIG. 8. This combination of the shaped piston 220 and the flexible walls of the capsule 210 assure that substantially all of the dental material, not shown in FIG. 7, contained within the capsule 210 is extruded.

Accordingly, in one embodiment of the present invention, the use of a transition surface and the relationship between the axes of the body portion, transition portion, and the discharge portion result in a substantial reduction of the extrusion force required to extrude high viscosity dental material. Additionally, the present invention permits the extrusion of dental material without shearing or damage to the dental material. This improves the performance of the dental material placed in a tooth for restoration. Accordingly, an improved restoration is formed. In another embodiment, flexible walls of the capsule cooperate with a shaped flexible piston to extrude substantial all of the dental material.

While the preferred embodiments of the present invention have been illustrated and described, it will be obvious to those skilled in the art that various modifications may be made without departing from the spirit and scope of this invention.

What is claimed is:

1. A dental capsule providing reduced extrusion forces comprising:
   a body portion having a substantially constant first inside diameter, a body portion inside surface, and a body portion axis;
   a transition portion, adjacent said body portion, having a reducing inside diameter and a transition portion axis, said body portion axis intersecting said transition portion axis forming a non-zero body-transition angle, said transition portion having an upper transition surface intersecting at an angle with the body portion inside surface of said body portion and a lower transition portion segment surface coincident with a straight line formed by the body portion inside surface; and
   a discharge portion having a substantially constant second inside diameter, adjacent said transition portion, and having a discharge portion axis, said transition portion axis intersecting said discharge portion axis forming a non-zero transition-discharge angle,
   whereby high viscosity dental material is capable of being extruded with reduced extrusion force and without damaging the high viscosity dental material.

2. A dental capsule as in claim 1 wherein:
   the body-transition angle ranges between twenty-five and thirty-five degrees; and the transition-discharge angle ranges between fifteen and twenty-five degrees.

3. A dental capsule as in claim 1 wherein:
the body-transition angle comprises substantially thirty degrees; and
the transition-discharge angle comprises substantially nineteen and one-half degrees.

4. A dental capsule as in claim 1 further comprising:
a flange attached to said body portion.

5. A dental capsule as in claim 1 wherein:
the dental capsule is made of a flexible material.

6. A dental capsule as in claim 1 further comprising:
a high viscosity dental material placed within said body portion.

7. A dental capsule as in claim 1 further comprising:
a sealing cap place on said discharge portion.

8. A dental capsule providing reduced extrusion forces comprising:
   a body portion having a substantially constant first inside diameter and a body portion axis;
   a transition portion, adjacent said body portion, having a reducing inside diameter and a transition portion axis, said body portion axis intersecting said transition portion axis forming a body-transition angle;
   a discharge portion having a substantially constant second inside diameter, adjacent said transition portion, and having a discharge portion axis, said transition portion axis intersecting said discharge portion axis forming a transition-discharge angle; and
   a flexible piston, said flexible piston comprising a cylindrical portion having a longitudinal length and a conical portion,
   whereby high viscosity dental material is ca able of being extruded with reduced extrusion force and without damaging the high viscosity dental material.

9. A dental capsule as in claim 8 further comprising:
a venting groove extending from said flange into said body portion the longitudinal length of the cylindrical portion of said flexible piston.

10. A dental capsule providing reduced extrusion forces for use with a high viscosity dental material comprising;
   a body portion having a substantially constant inside diameter, a body portion inside surface, and a body portion axis;
   a transition portion, adjacent said body portion, having a reducing inside diameter and a transition portion axis, said body portion axis intersecting said transition portion axis forming a body-transition angle, the body-transition angle ranging between twenty-five and thirty-five degrees, said transition portion having an upper transition surface intersecting at an angle with the body portion inside surface of said body portion and a lower transition portion segment surface coincident with a straight line formed by the body portion inside surface; and
   a discharge portion, adjacent said transition portion, having a discharge portion axis, said transition portion axis intersecting said discharge portion axis forming a transition-discharge angle, the transition-discharge angle ranging between fifteen and twenty-five degrees,
   whereby high viscosity dental material is capable of being extruded with reduced extrusion force and without damaging the high viscosity dental material.

11. A dental capsule providing reduced extrusion forces for use with a high viscosity dental material as in claim 10 wherein:
   the body-transition angle comprises substantially thirty degrees; and
   the transition-discharge angle comprises substantially nineteen and one-half degrees.

12. A dental capsule providing reduced extrusion forces for use with a high viscosity dental material comprising:
   a body portion having a substantially constant inside diameter and a body portion axis;
   a transition portion, adjacent said body portion, having a reducing inside diameter and a transition portion axis, said body portion axis intersecting said transition portion axis forming a body-transition angle, the body-transition angle ranging between twenty-five and thirty-five degrees;
   a discharge portion, adjacent said transition portion, having a discharge portion axis, said transition portion axis intersecting said discharge portion axis forming a transition-discharge angle, the transition-discharge angle ranging between fifteen and twenty-five degrees;
   a flexible piston, said flexible piston comprising a cylindrical portion having a longitudinal length and a conical portion; and
   a venting groove extending from said flange into said body portion the longitudinal length of the cylindrical portion of said flexible piston,
   whereby high viscosity dental material is capable of being extruded with reduced extrusion force and without damaging the high viscosity dental material.

13. A dental capsule providing reduced extrusion forces for use with a high viscosity dental material comprising:
   a body portion having a substantially constant inside diameter and a body portion axis;
   a high viscosity dental material placed within said body portion;
   a flange attached to said body portion;
   a transition portion, adjacent said body portion, having a reducing inside diameter and a transition portion axis, said body portion axis intersecting said transition portion axis forming a body-transition angle, the body-transition angle ranging between twenty-five and thirty-five degrees;
   a discharge portion, adjacent said transition portion, having a discharge portion axis, said transition portion axis intersecting said discharge portion axis forming a transition-discharge angle, the transition-discharge angle ranging between fifteen and twenty-five degrees;
   a flexible piston, said flexible piston comprising a cylindrical portion having a longitudinal length and a conical portion;
   a venting groove extending from said flange into said body portion the longitudinal length of the cylindrical portion of said flexible piston; and
   a cap sealing said discharge portion,
   whereby high viscosity dental material is capable of being extruded with reduced extrusion force and without damaging the high viscosity dental material.

14. A dental capsule for completely extruding a high viscosity dental material comprising:
   a cylindrical body portion made of a flexible material;
   a flange adjacent one end of said cylindrical body portion;
   a curved discharge portion made of a flexible material adjacent another end of said cylindrical body portion, said curved discharge portion having a reducing diameter; and a piston made of a flexible material comprising a cylindrical portion having a longitudinal length and a conical portion, the conical portion having a smallest diameter that is larger than a smallest diameter of the reducing diameter of said curved discharge portion, whereby said piston negotiates said curved discharge portion with reduced extrusion force and extrudes substantial all of the high viscosity dental material and said curved discharge portion and said piston are caused to change shape.

15. A dental capsule for completely extruding a high viscosity dental material as in claim 14 further comprising:

a venting groove extending from said flange into said body portion the longitudinal length of the cylindrical portion of said flexible piston.

16. A dental capsule for completely extruding a high viscosity dental material as in claim 15 further comprising:

a high viscosity dental material placed within said cylindrical body portion.

17. A dental capsule providing reduced extrusion forces used in dispensing a high viscosity dental material comprising:

a body portion having a substantially constant first inside diameter and a body portion axis;

a transition portion, adjacent said body portion, having a reducing inside diameter and a transition portion axis, said body portion axis intersecting said transition portion axis forming a body-transition angle;

a discharge portion having a substantially constant second inside diameter, adjacent said transition portion, and having a discharge portion axis, said transition portion axis intersecting said discharge portion axis forming a transition-discharge angle;

wherein the body-transition angle ranges between twenty-five and thirty-five degrees and the transition-discharge angle ranges between fifteen and twenty-five degrees;

a high viscous dental material placed within said body portion; and a piston having a flexible conical front portion with a small diameter placed within said body portion, wherein the small diameter of said piston is smaller than the diameter of the substantially constant second inside diameter of said discharge portion, whereby the flexible conical front portion is sufficiently flexible to negotiate around said transition portion and said high viscosity dental material is capable of being extruded with reduced extrusion force and without damaging said high viscosity dental material.

* * * * *